(12) United States Patent
Kim et al.

(10) Patent No.: US 9,637,422 B2
(45) Date of Patent: May 2, 2017

(54) METHOD FOR PREPARING HIGH PURITY ISOBUTENE USING GLYCOLETHER

(75) Inventors: Myeong-Seok Kim, Daejon (KR); Jae-Hoon Uhm, Daejeon (KR); Min-Sup Park, Daejeon (KR); Hyoung-Jae Seo, Daejeon (KR); Kyoung-Tae Min, Daejeon (KR)

(73) Assignee: DAELIM INDUSTRIAL CO., LTD., Seoul (KR)

( * ) Notice: Subject to any disclaimer, the term of this patent is extended or adjusted under 35 U.S.C. 154(b) by 334 days.

(21) Appl. No.: 14/000,095

(22) PCT Filed: Feb. 17, 2012

(86) PCT No.: PCT/KR2012/001214
§ 371 (c)(1),
(2), (4) Date: Aug. 16, 2013

(87) PCT Pub. No.: WO2012/112003
PCT Pub. Date: Aug. 23, 2012

(65) Prior Publication Data
US 2013/0324781 A1    Dec. 5, 2013

(30) Foreign Application Priority Data

Feb. 18, 2011 (KR) .................. 10-2011-0014521

(51) Int. Cl.
*C07C 1/22* (2006.01)
*C07B 37/06* (2006.01)
*C07C 1/20* (2006.01)
*C07C 41/06* (2006.01)

(52) U.S. Cl.
CPC ................ *C07C 1/22* (2013.01); *C07B 37/06* (2013.01); *C07C 1/20* (2013.01); *C07C 41/06* (2013.01); *C07C 2531/10* (2013.01); *Y02P 20/582* (2015.11)

(58) Field of Classification Search
USPC .................. 585/639, 640, 641, 638
See application file for complete search history.

(56) References Cited

U.S. PATENT DOCUMENTS

| 5,146,041 A | 9/1992 | Knifton |
| 5,177,301 A * | 1/1993 | Knifton ............... C07C 7/14891 568/697 |
| 5,849,971 A | 12/1998 | Sakuth et al. |

FOREIGN PATENT DOCUMENTS

| EP | 0530966 A2 | 3/1993 |
| EP | 0669307 A1 | 8/1995 |
| FR | 0796156 | 3/1936 |
| JP | S55-064534 | 5/1980 |
| JP | S56-010124 | 2/1981 |
| JP | S59-051224 | 3/1984 |
| JP | S63-027445 | 2/1988 |
| JP | H10-101606 | 4/1998 |
| JP | H11-193255 | 7/1999 |

OTHER PUBLICATIONS

Written Opinion of PCT/ISA/237 with English translation.

* cited by examiner

*Primary Examiner* — Sharon Pregler
(74) *Attorney, Agent, or Firm* — Hesin Rothenberg Farley & Mesiti P.C.

(57) ABSTRACT

Disclosed is a method of preparing isobutene in which high-purity isobutene is separated (prepared) from a $C_4$ mixture by cracking glycol ether prepared from a $C_4$ mixture (in particular, $C_4$ raffinate-1) containing isobutene and a glycol. The method includes cracking glycol ether into isobutene and glycol at a temperature between 50° C. and 300° C. in the presence of a strongly acidic catalyst. The glycol ether may be prepared by reaction between a $C_4$ mixture containing isobutene and glycol in the presence of an acid catalyst.

7 Claims, 1 Drawing Sheet

METHOD FOR PREPARING HIGH PURITY ISOBUTENE USING GLYCOLETHER

CROSS REFERENCE to RELATED APPLICATIONS

This application is a national stage filing under section 371 of International Application No. PCT/KR2012/001214 filed Feb. 17, 2012 and published as WO 2012/112003, and claims priority to Korean Patent Application No. 10-2011-0014521 filed on Feb. 18, 2011, the entire disclosure of these applications being hereby incorporated herein by reference.

TECHNICAL FIELD

The present invention relates to a method of preparing high-purity isobutene using glycol ether and, more particularly, to a method of preparing isobutene whereby high-purity isobutene is separated (prepared) from a $C_4$ mixture by cracking glycol ether prepared from a $C_4$ mixture (in particular, $C_4$ raffinate-1) containing isobutene and glycol.

BACKGROUND ART

Isobutene is an important industrial raw material and has recently received attention as a raw material of butyl rubber, polyisobutylene, isobutene oligomer, and methylmethacrylate (MMA). Isobutene is generally present as a mixture of an unsaturated hydrocarbon such as butadiene, N-butene or the like and a saturated hydrocarbon such as N-butane, isobutane, or the like. Thus, to use isobutene as a raw material, isobutene needs to be separated from the $C_4$ mixture.

In general, as a raw material stream for industrial application used to prepare isobutene, $C_4$ raffinate-1 remaining after separation of butadiene by extraction or extractive distillation in a first step of a post-treatment process of a $C_4$ mixture produced by cracking naphtha may be used. $C_4$ raffinate-1 is a hydrocarbon mixture containing olefins, i.e., isobutene, 1-butene and 2-butene (cis and trans) and saturated hydrocarbons, i.e., N-butane and isobutane. Among these materials, 1-butene has small difference in boiling point from isobutene and thus cannot be economically separated from the hydrocarbon mixture by distillation.

As a method of preparing (separating) isobutene from $C_4$ raffinate-1, a t-butyl alcohol (TBA) dehydration method using hydration and dehydration in combination, a methyl t-butyl ether (MTBE) cracking method in which isobutene is obtained by adding methanol to isobutene using an acid catalyst and cracking the methanol-added isobutene, an isobutane dehydrogenation method, or the like may be used.

The isobutane dehydrogenation method generally uses a catalyst such as a Group VIII noble metal, tin, zeolite, or the like. In this regard, when dehydrogenation for preparation of isobutene is performed, isomerization and cracking, which are side reactions, simultaneously occur, and byproducts generated by the side reactions reduce activity of the catalyst, shortening lifetime thereof, and making separation of isobutene difficult. To address these problems, U.S. Pat. Registration No. 4,727,216 discloses a method of minimizing byproduct and easily removing byproduct by using a sulfided type L zeolite catalyst. However, the method is suitable for use in a case in which a large amount of pure isobutane is used as a raw material and thus is not economical and it is deemed that it is impossible to use a great amount of pure isobutane as a raw material in an actual production process.

Isobutene can be easily converted into a derivative thereof by water or alcohol, and thus, the TBA dehydration method and the MTBE cracking method, in which isobutene is selectively obtained from a $C_4$ mixture by addition of water or alcohol, may be generally used as a method of preparing (separating) isobutene from $C_4$ raffinate-1.

The TBA dehydration method is a method in which isobutene of $C_4$ raffinate-1 is subjected to hydration reaction to prepare TBA, the TBA is separated, and then the separated TBA is subjected to dehydration to obtain isobutene. As a hydration reaction method of isobutene, Japanese Patent Application Laid-open Nos. Sho 56-10124, 56-2855 and 55-64534 disclose a method of preparing TBA from isobutene through rechargeable fixed-bed reaction using a strongly acidic ion exchange resin. In the hydration reaction method, a catalyst is fixed and thus separation of isobutene from the catalyst is good, whereas contact efficiency is low and thus reactivity is low. In addition, Japanese Patent Application Laid-open No. Heisei 11-193255 discloses a method of enhancing reactivity of the hydration reaction method and hydration reaction selectivity through use of an appropriate solvent and optimal cycling. However, this method is fundamentally disadvantageous in that hydrocarbon and water as reaction raw materials are not mixed and most of a product needs to be cycled.

In addition, the TBA dehydration to obtain isobutene from TBA generally uses a strong acid such as sulfuric acid or the like as a catalyst, and thus, a manufacturing apparatus that is resistant to corrosion of a strong acid is needed and waste sulfuric acid discharged after dehydration needs to be treated. To address these problems, dehydration may be performed using, as a catalyst, a strongly acidic ion exchange resin containing a sulfonic acid group. In this method, however, when reaction temperature is low, a composition ratio of water after reaction increases and thus reaction rate is significantly decreased. On the other hand, when reaction temperature is high, isobutene as a reaction product is produced in large amounts, which results in production of large amounts of byproducts. With regards to this, U.S. Pat. No. 5,849,971 discloses an enhanced method through use of a reactive distillation column, as compared to existing methods.

The MTBE cracking method is a method whereby MTBE is prepared by etherification of isobutene of $C_4$ raffinate-1 with methanol, the prepared MTBE is separated, and the separated MTBE is subjected to cracking (decomposition) to obtain isobutene. MTBE is a fuel component useful for engines of four-wheel vehicles to increase octane number, and addition reaction of methanol to isobutene in $C_4$ raffinate-1 is substantially faster than addition reaction of water. For this reason, the MTBE cracking method is most widely used for industrial application, and MTBE is widely used as an inexpensive precursor to obtain high-purity isobutene.

U.S. Pat. No. 5,567,860 discloses preparation of MTBE and a method of preparing high-purity isobutene from a $C_4$ mixture through cracking of MTBE. According to the method, MTBE, 2-methoxy butane (MSBE), an unreacted $C_4$ mixture, methanol, water, DME, isobutene oligomer, and the like may be obtained by etherification of a $C_4$ mixture containing isobutene with methanol, and, when the compounds are subjected to fractional distillation using a column, low boiling point materials including $C_4$ hydrocarbon (unreacted $C_4$ mixture), methanol and DME and high boiling point materials including $C_4$ oligomer (isobutene oligomer) may be obtained. MTBE and MSBE are obtained from a side stream taken from the column and cracked through a cracking process using an acid catalyst, thereby preparing isobutene. In the cracking reaction (process), however, main components, i.e., isobutene, N-butene, and methanol are obtained together with non-cracked MTBE and MSBE. Thus, the mixtures need to be separated by distillation, and a $C_4$/methanol azeotrope containing isobutene and N-butene and DME is separated as a low boiling point component. In addition, to obtain high-purity isobutene, the separation process requires washing and distillation one or more times. The method of preparing isobutene from MTBE is complicated in that accompanying materials in the $C_4$ mixture and unreacted reaction products or byproducts obtained through etherification and cracking in plural columns and a washing process have to be removed to obtain high-purity isobutene. For example, DME and $C_4$ oligomer as byproducts have to be treated and methanol and MTBE, which form an azeotrope, have to be recycled to obtain high yield.

DISCLOSURE

Technical Problem

Therefore, the present invention has been made in view of the above problems, and it is an object of the present invention to provide a method of preparing isobutene in which high-purity isobutene may be prepared from glycol ether that is prepared from a $C_4$ mixture with high selectivity and thus contains no impurities and has high reactivity, using a simplified and economical manufacturing process.

Technical Solution

In accordance with an aspect of the present invention, the above and other objects can be accomplished by the provision of a method of preparing isobutene, including cracking glycol ether into isobutene and glycol at a temperature between 50° C. and 300° C. in the presence of a strongly acidic catalyst. The glycol ether may be prepared by reacting a $C_4$ mixture containing isobutene with glycol in the presence of an acid catalyst.

Advantageous Effects

The isobutene preparation method according to the present invention may be used to economically prepare isobutene through simplified manufacturing processes by preparing, from a $C_4$ mixture such as $C_4$ raffinate-1 or the like, glycol ether that can be stably prepared in high yield and with high selectivity without production of byproducts and by using the prepared glycol ether as a precursor of isobutene. In addition, the isobutene preparation method uses an industrially widely used acid catalyst and strongly acidic catalyst, does not incur generation of wastewater due to no extraction process, is performed by simplified manufacturing processes, and has no loss in raw materials, and thus, energy and raw material costs may be more innovatively reduced. Moreover, a reactive distillation column that enables simultaneous implementation of decomposition and distillation is used when isobutene is decomposed and thus raw material costs may further be reduced.

DESCRIPTION OF DRAWINGS

The above and other objects, features and other advantages of the present invention will be more clearly understood from the following detailed description taken in conjunction with the accompanying drawings, in which.

DETAILED DESCRIPTION

Figure 1:
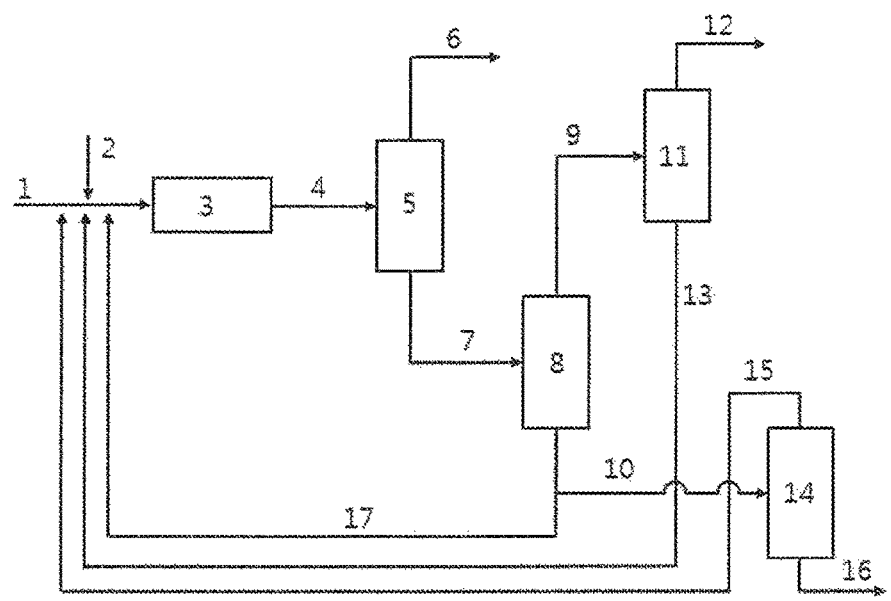
FIG. 1 is a schematic block diagram for explaining an isobutene preparation method according to an embodiment of the present invention.

Hereinafter, the present invention will be described in detail with reference to the accompanying drawings.

An isobutene preparation method according to the present invention involves separation (preparation) of high-purity isobutene from a $C_4$ mixture and includes cracking glycol ether into isobutene and glycol at a temperature between 50° C. and 300° C. in the presence of a strongly acidic catalyst.

The strongly acidic catalyst used herein may be a general, commercially available strongly acidic catalyst having a Hammett (Ho) acidity function of +1.5 or less. In this regard, the Hammett acidity function is the most common means of quantitatively measuring acidity of a solid acid. For example, the strongly acidic catalyst may be a clay-based solid catalyst, zeolite, silica-alumina, an ion exchange resin, a heteropoly compound, or the like, preferably a clay-based solid catalyst having a Ho acidity function of less than −3.0. As the clay-based solid catalyst, Shacnite #136 (manufacturer: Daeil Chemical, Co., Ltd), which is an industrially economical clay-based strongly acidic catalyst, may be used. Shacnite #136 is prepared by forming a surface with fine pores through elution of a soluble material in the structure by activation treatment, is of a granular type, and has a pore diameter of 30 to 50 Å and a specific surface area of 150 to 300 $m^2$/g. In this regard, specific surface area, porosity, stability, swelling properties, contractibility, or the like of the strongly acidic catalyst may vary according to preparation methods.

Cracking of glycol ether into isobutene and glycol may be continuously or non-continuously performed on an acid catalyst (strongly acidic catalyst) located on a fixed bed. For example, cracking may be performed in a glycol ether cracking reactor or a reactive distillation column. As the glycol ether cracking reactor, a fixed bed reactor, a shell and tube reactor, a kettle reactor, and the like may be used alone or in combination. When at least one cracking reactor or reactive distillation column is used, the cracking reactor and reactive distillation column may be used in series, in parallel, or in combination thereof.

In addition, the cracking of glycol ether into isobutene and glycol may be performed, for example, at a pressure between 0 kgf/$cm^2$ and 20 kgf/$cm^2$ and at a temperature between 50° C. and 300° C., preferably between 70° C. and 200° C., and more preferably between 100° C. and 150° C. The cracking reaction is a thermodynamically equilibrium reaction and, as cracking reaction temperature increases, cracking reaction rate increases. When the cracking reaction temperature is less than 50° C., the cracking reaction rate is too slow or glycol ether may not be cracked into isobutene and glycol. On the other hand, when the cracking reaction temperature exceeds 300° C., addition reaction may occur in the produced isobutene.

The glycol ether used herein may be general glycol t-butyl ether, preferably glycol ether prepared by reaction between a $C_4$ mixture containing isobutene and glycol in the presence of an acid catalyst.

The acid catalyst may be a general, commercially available acid catalyst having a Hammett (Ho) acidity function of +1.5 or less, which is the most common means of quantitatively measuring acidity of a solid acid. For example, the acid catalyst may be a polymer resin catalyst such as a clay-based solid catalyst, zeolite, silica-alumina, an ion exchange resin, a heteropoly compound, a strongly acidic solid ion exchange resin containing a sulfonic acid group, or the like. Preferably, the acid catalyst may be a strongly acidic solid ion exchange resin containing a sulfonic acid group. As the strongly acidic solid ion exchange resin, Amberlyst 15 (manufacturer: Rohm&Hass) may be used. Amberlyst 15 is a bead-type ion exchange resin, and has a particle size of 0.6 to 0.85 mm, a pore diameter of 300 Å, and a specific surface area of 53 m$^2$/g.

The $C_4$ mixture containing isobutene ($C_4$ hydrocarbon mixture) may be a $C_4$ mixture containing 10 wt % or more of isobutene. Preferably, the $C_4$ mixture containing isobutene may be $C_4$ raffinate-1 remaining after extraction of 1,3-butadiene from $C_4$ raw materials, which are $C_4$ olefin components obtained through decomposition of naphtha. $C_4$ raffinate-1 contains paraffins such as isobutane and normal butane and olefins such as 1-butene, 2-butene, isobutene, and the like, and a content of isobutene is between about 30 wt % and about 50 wt %. In addition, as the $C_4$ mixture containing isobutene, a butane-butene (B-B) fraction, which is a $C_4$ mixture obtained through a petroleum refining process, may be used.

The glycol used herein may be a general glycol compound, for example, a compound represented by Formula 1 below. In addition, the glycol may be obtained by recycling of glycol separated through the cracking of glycol ether:

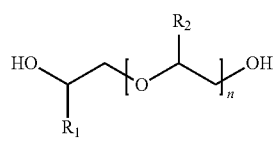

<Formula 1> wherein $R_1$ and $R_2$ are each independently a hydrogen atom or a $C_1$-$C_5$ alkyl group, and n is an integer of 0 to 4.

The glycol ether may be prepared through continuous reaction in a general fixed bed type glycol ether reactor by continuously supplying the $C_4$ mixture and glycol to the glycol ether reactor in the presence of the acid catalyst. For example, the glycol ether may be prepared through two-step reaction as illustrated in Reaction Scheme 1 below. In this regard, the amounts of the glycol and isobutene of the $C_4$ mixture supplied are not particularly limited, but the glycol and the isobutene may be supplied, for example, in a molar ratio of 1:1 to 5:1 (glycol: isobutene). In the first step, selective reaction between glycol (e.g., EG) and isobutene of the $C_4$ mixture ($C_4$ raffinate-1) occurs in the presence of the acid catalyst to generate ethylene glycol mono-t-butyl ether (ETB). In the second step, selective reaction between the intermediate product (i.e., ETB) and isobutene occurs in the presence of the acid catalyst to generate ethylene glycol di-t-butyl ether (DBE). In this regard, EG is used as the glycol in Reaction Scheme 1, but, even when other glycols are used, each glycol ether (glycol t-butyl ether) may be prepared through the same mechanism.

In the two-step reaction, which is an exothermic reaction, as reaction temperature decreases, an equilibrium conversion rate increases while a reaction rate is significantly reduced. Thus, to implement efficient preparation, the two-step reaction may be performed at a reaction temperature between 20° C. and 150° C., preferably between 20° C. and 100° C., and more preferably between 30° C. and 60° C. In addition, the reaction may be performed at a reaction pressure between 0.1 kgf/cm$^2$ and 30 kgf/cm$^2$, preferably between 0.2 kgf/cm$^2$ and 20 kgf/cm$^2$, and more preferably between 0.5 kgf/cm$^2$ and 15 kgf/cm$^2$. Table 1 below shows equilibrium conversion rates of ETB according to temperature, and Table 2 below shows equilibrium conversion rates of DBE according to temperature (rate constant: [m$^3$/kmol/hr], $k_1$: 2.48×10^8EXP(−10820/RT), $k_{-1}$: 7.94×10^14EXP(−21900/RT), $k_2$: 2.02×10^7EXP(−10680/RT), $k_{-2}$: 7.48×10^14EXP(−22500/RT)).

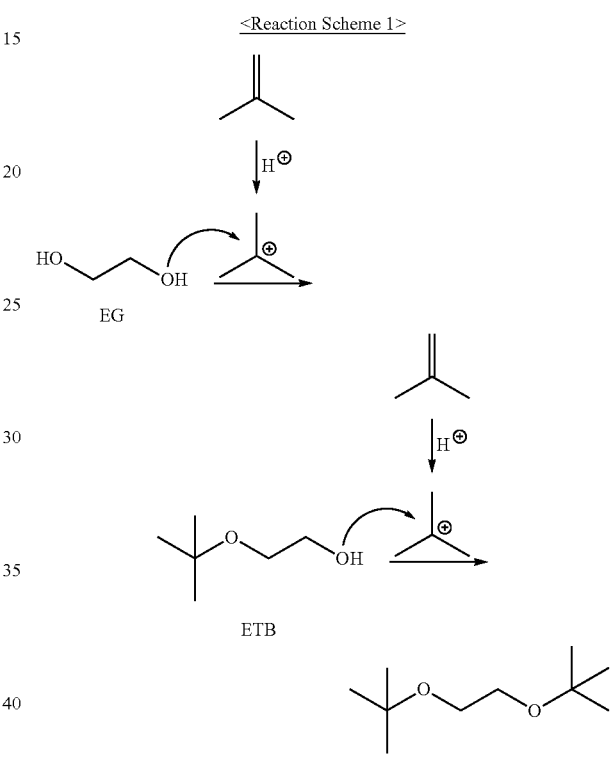

<Reaction Scheme 1>

TABLE 1

| Temperature (° C.) | Rate constant ($k_1$) | Rate constant ($k_{-1}$) | Equilibrium constant ($K_e$) | Equilibrium conversion rate (%) |
|---|---|---|---|---|
| 20 | 2.115 | 0.035 | 61.2 | 99.0 |
| 40 | 6.933 | 0.384 | 18.1 | 97.0 |
| 60 | 19.706 | 3.191 | 6.2 | 93.4 |
| 80 | 49.758 | 20.869 | 2.4 | 89.2 |
| 100 | 113.758 | 111.603 | 1.0 | 86.1 |
| 120 | 239.084 | 503.185 | 0.48 | 84.2 |
| 140 | 467.603 | 1960.805 | 0.24 | 83.3 |
| 150 | 638.572 | 3688.423 | 0.17 | 83.0 |

TABLE 2

| Temperature (° C.) | Rate constant ($k_2$) | Rate constant ($k_{-2}$) | Equilibrium constant ($K_e$) | Equilibrium conversion rate (%) |
|---|---|---|---|---|
| 20 | 0.220 | 0.012 | 17.8 | 97.5 |
| 40 | 0.708 | 0.146 | 4.9 | 92.9 |

TABLE 2-continued

| Temperature (° C.) | Rate constant ($k_2$) | Rate constant ($k_{-2}$) | Equilibrium constant ($K_e$) | Equilibrium conversion rate (%) |
|---|---|---|---|---|
| 60 | 1.986 | 1.282 | 1.5 | 86.9 |
| 80 | 4.955 | 8.780 | 0.56 | 82.3 |
| 100 | 11.207 | 49.121 | 0.23 | 80.0 |
| 120 | 23.328 | 230.218 | 0.10 | 78.9 |
| 140 | 45.227 | 929.042 | 0.05 | 78.4 |
| 150 | 61.513 | 1176.225 | 0.03 | 78.3 |

In preparation of glycol ether according to Reaction Scheme 1, reverse reaction is inhibited to convert ETB produced in the first step into DBE, and weight hourly space velocity (WHSV) may be adjusted to 1 to 3 at a low temperature between 30° C. and 50° C. to increase conversion rate. In addition, when the acid catalyst is used in the glycol ether preparation reaction, there is small reduction in reaction activity even after long-term reaction, accumulation due to production of impurities does not occur, and glycol ether may be stably and continuously produced in high yield.

To separate (prepare) high-purity isobutene from the $C_4$ mixture according to the isobutene preparation method according to the present invention, for example, a fraction a) containing glycol ether (e.g., ETB and/or DBE, DETB and/or DDBE, or the like), unreacted glycol, an unreacted $C_4$ mixture, and the like is obtained by reacting a $C_4$ mixture (e.g., $C_4$ raffinate-1 or the like) with glycol (e.g., EG, DEG, or the like) (step (i)), the glycol ether (e.g., ETB and/or DBE, DETB and/or DDBE, or the like) present in the fraction a) is cracked into isobutene and glycol (e.g., EG, DEG, or the like) (step (ii)), and high-purity isobutene is obtained by separating the isobutene and glycol produced in step (ii) and the separated glycol is recycled as a raw material (step (iii)).

FIG. 1 is a schematic block diagram for explaining an isobutene preparation method according to an embodiment of the present invention. As illustrated in FIG. 1, a $C_4$ mixture 1 (e.g., $C_4$ raffinate-1 or the like) and glycol 2 (e.g., EG, DEG, or the like) are supplied to a glycol ether polymerization reactor 3, and a reaction product mixture stream 4 containing glycol ether (e.g., ETB and/or DBE, DETB and/or DDBE, or the like), unreacted glycol, unreacted $C_4$ mixture, and the like is supplied to a first distillation column (a $C_4$ distillation column 5) from the glycol ether polymerization reactor 3. The unreacted $C_4$ mixture is separated and discharged as an unreacted $C_4$ mixture stream 6 from the first distillation column 5, and a reaction product mixture stream 7 from which the unreacted $C_4$ mixture has been removed is supplied to a second distillation column (i.e., a glycol ether distillation column 8) for separation of the base product. In this regard, among the glycol ether, main products, i.e., dialkyl ethers (DBE, DDBE, and the like) and monoalkyl ethers (ETB, DETB, and the like), form an azeotrope. The monoalkyl ethers are all separated as a glycol ether stream 9, which is an upper stream, together with the dialkyl ethers when a large amount of dialkyl ethers is distilled. The glycol ether stream 9 may be supplied to a glycol ether cracking reactor 11 and then cracked into pure isobutene 12 and glycol 13. The dialkyl ether may be completely cracked in the glycol ether cracking reactor 11, and a remaining portion of the monoalkyl ether that has not been cracked may be recycled to the glycol ether polymerization reactor 3 together with the glycol 2 to be polymerized as dialkyl ether. Lower streams (regenerated glycol streams 10 and 17) of the second distillation column 8 mostly consist of glycol and may be recycled to the glycol ether polymerization reactor 3 or, as desired, may be supplied to a third distillation column (a distillation column 14 for regeneration of glycol) to be further separated into pure glycol 15 and then be recycled to the glycol ether polymerization reactor 3. The third distillation column 14 may separate thermally deformed glycol generated when glycol is recycled for a long period of time to obtain the pure glycol 15, and the thermally deformed glycol is separated and discharged through a deformed glycol stream 16.

In this regard, a general temperature-controllable fixed-bed reactor or the like may be used as the glycol ether polymerization reactor 3 and the glycol ether cracking reactor 11, and a general multi-stage (e.g., 10 to 50 theoretical plate) distillation column of a packing or tray type may be used as the first, second and third distillation columns 5, 8 and 14. In the first distillation column 5, separation of the unreacted $C_4$ mixture stream 6 and the reaction product mixture stream 7 from which the unreacted $C_4$ mixture has been removed may be performed at a pressure between 0.1 kgf/$cm^2$ and 30 kgf/$cm^2$ and a temperature between 20° C. and 250° C., preferably at a pressure between 3 kgf/$cm^2$ and 10 kgf/$cm^2$ and a temperature between 40° C. and 200° C. In addition, separation of the glycol ether 8 and the glycols 10 and 17 in the second distillation column 8 may be performed at a pressure between 0.1 kgf/$cm^2$ and 1 kgf/$cm^2$ and a temperature between 200° C. and 300° C., preferably at a pressure between 0.1 kgf/$cm^2$ and 0.5 kgf/$cm^2$ and a temperature between 220° C. and 250° C. Separation of the pure glycol 15 and the deformed glycol stream 16 in the third distillation column 14 may be performed at a pressure between 0.1 kgf/$cm^2$ and 10 kgf/$cm^2$ and a temperature between 100° C. and 300° C., preferably at a pressure between 0.5 kgf/$cm^2$ and 3 kgf/$cm^2$ and a temperature between 200° C. and 250° C.

Figure 2:
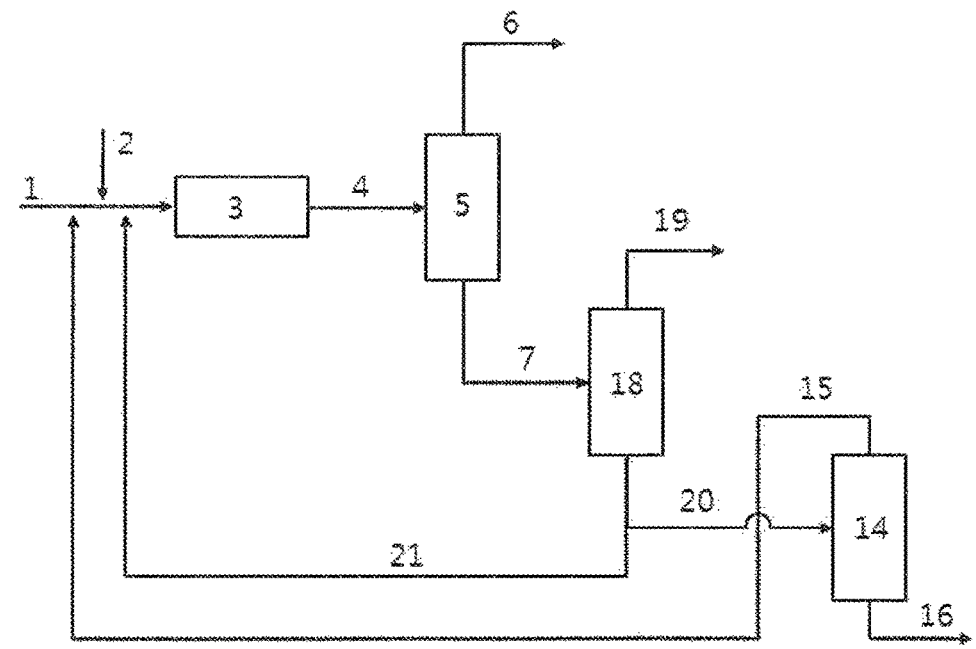
FIG. 2 is a schematic block diagram for explaining an isobutene preparation method according to another embodiment of the present invention.

FIG. 2 is a schematic block diagram for explaining an isobutene preparation method according to another embodiment of the present invention. As illustrated in FIG. 2, the isobutene preparation method according to the present embodiment may use at least one reactive distillation column 18 instead of the second distillation column 8 and the glycol ether cracking reactor 11. The reactive distillation column 18 is prepared by forming a catalyst layer in a general multi-stage distillation column (by packing the multi-stage distillation column with a strongly acidic catalyst), and separation of isobutene through decomposition and distillation of glycol ether may be simultaneously performed in the reactive distillation column 18 and thus raw material costs may further be reduced. Lower streams (regenerated glycol streams 20 and 21) of the reactive distillation column 18 mostly consist of glycol and may be recycled to the glycol ether polymerization reactor 3 or, as desired, may be supplied to the third distillation column (the distillation column 14 for regeneration of glycol) to be further separated into the pure glycol 15 and then be recycled to the glycol ether polymerization reactor 3. In addition, thermally deformed glycol is separated and discharged through the deformed glycol stream 16.

According to the isobutene preparation method, glycol ether having high reactivity as a cracking precursor of isobutene may be prepared from a $C_4$ mixture with high selectivity without production of impurities. In addition, isobutene may be economically prepared from glycol ether through a simplified preparation process that does not require an impurity removal process.

MODE FOR INVENTION

Hereinafter, the present invention will be described more fully with reference to the following examples. These examples are provided for illustrative purposes only and should not be construed as limiting the scope and spirit of the present invention.

EXAMPLES 1 TO 7

Preparation of Isobutene

As the glycol ether polymerization reactor 3, 100 g of a strongly acidic solid ion exchange resin (Product name: Amberlyst 15, manufacturer: Rohm&Hass) as an acid catalyst packed into a vertical tubular reactor (made of SUS316), provided at an outer side thereof with an oil heating bath and having an inner diameter of 25.4 mm and a length of 100 cm, was used. As the first distillation column ($C_4$ distillation column 5), a distillation column having a theoretical plate number of 15 was used. In addition, a distillation column having a theoretical plate number of 30 was used as the second distillation column (glycol ether distillation column 8) used to separate glycol ether, and 100 g of a strongly acidic solid catalyst (Product name: Shacnite #136, manufacturer: Daeil Chemical, Co., Ltd) packed into a vertical tubular reactor (SUS316), provided at an outer side thereof with an oil heating bath and having an inner diameter of 25.4 mm and a length of 100 cm, was used as the glycol ether cracking reactor 11. As the third distillation column (distillation column 14 for regeneration of glycol) used to regenerate pure glycol, a distillation column having a theoretical plate number of 10 was used. The glycol ether polymerization reactor 3 and the glycol ether cracking reactor 11 had a double tubular shape and were used to control reaction temperature by cycling heat transfer oil of the oil heating bath via an outer tube thereof.

The glycol ether polymerization reactor 3 was preheated to a temperature between 50° C. and 60° C. before reaction, the glycol ether cracking reactor 11 was preheated to a temperature between 100° C. and 150° C. before reaction, and a pressure in the reaction tube was 3 kgf/cm$^2$.

To prepare glycol ether (ethylene glycol di-t-butyl ether (DBE)) and ethylene glycol mono-t-butyl ether (ETB), C4 raffinate-1 having compositions shown in Table 3 below and ethylene glycol (EG) were supplied to a lower portion of the glycol ether polymerization reactor 3. In addition, according to reaction conditions shown in Table 4 below, reaction was performed at a WHSV of 1.0 to 3.0 (hr$^{-1}$) based on $C_4$ raffinate-1, in a molar ratio of EG to isobutene of 2.0, and a reaction tube pressure of 10 kgf/cm$^2$. In the product mixture produced through the reaction, unreacted $C_4$ mixture ($C_4$ raffinate-1, 6) was separated and discharged via the first distillation column 5 and then the reaction product mixture stream 7 from which the unreacted $C_4$ mixture has been removed was supplied to the second distillation column 8, to obtain the glycol ether stream 9 as a base product (a large amount of DBE and a small amount of ETB). Next, the obtained DBE and ETB were supplied to the glycol ether cracking reactor 11, and glycol ether was cracked according to the reaction conditions shown in Table 4 below, to obtain isobutene 12. In this regard, the EGs 10, 13 and 17 separated from the second distillation column 8 and the glycol ether cracking reactor 11 were recycled as reactants to the glycol ether polymerization reactor 3, or were supplied to the third distillation column 14 to remove the thermally deformed EG 16, followed by recycling of the pure EG 15. The unreacted $C_4$ mixture ($C_4$ raffinate-1, 6) was analyzed by gas chromatography (Device name: Agilent 7890A) to obtain reaction conversion rates of DBE and ETB into isobutene. Results are shown in Table 4 below.

TABLE 3

| Component | Isobutene | 1-butene | Cis-2-butene | Trans-2-butene | Isobutane | N-butane |
|---|---|---|---|---|---|---|
| Wt % | 49.6 | 23.1 | 4.3 | 9.1 | 3.1 | 10.8 |

TABLE 4

| | Example 1 | Example 2 | Example 3 | Example 4 | Example 5 | Example 6 | Example 7 |
|---|---|---|---|---|---|---|---|
| WHSV (hr$^{-1}$) | 3 | 3 | 3 | 2 | 2 | 2 | 1 |
| Molar ratio of EG/isobutene | 2.0 | 2.0 | 2.0 | 2.0 | 2.0 | 2.0 | 2.0 |
| Reaction temperature (° C.) | 60 | 60 | 40 | 60 | 50 | 40 | 40 |
| Reaction pressure (kgf/cm$^2$) | 10 | 10 | 10 | 10 | 10 | 10 | 10 |
| Conversion rate of isobutene (%) | 88 | 88 | 90 | 91 | 92 | 94 | 96 |
| Weight ratio of DBE/ETB | 2.7 | 2.7 | 3.0 | 3.2 | 3.6 | 3.7 | 4.0 |
| Cracking temperature (° C.) | 125 | 150 | 150 | 150 | 150 | 150 | 150 |
| Cracking pressure (kgf/cm$^2$) | 3 | 3 | 3 | 3 | 3 | 3 | 3 |
| Cracking yield of isobutene (%) | 77 | 84 | 86 | 89 | 90 | 91 | 93 |

From results shown in Table 4 above, it can be confirmed that production of DBE increases as reaction temperature decreases, and isobutene yield increases as cracking temperature increases. From results of Examples 1 and 2, it can be confirmed that isobutene cracking yield increases as cracking temperature increases and, from results of Examples 4 and 5, it can be confirmed that the amount of DBE produced increases as reaction temperature decreases. In addition, reaction rate (production rate) of DBE is slower than production rate of ETB, and thus, from results of Examples 3, 6 and 7, it can be confirmed that the amount of DBE produced increases as the WHSV is kept low.

From the results, it can be confirmed that the isobutene preparation method according to the present invention uses glycol ether as a precursor that can be prepared in high yield and with high selectivity and thus isobutene may be prepared in high yield and with high selectivity, reaction processes may be simplified due to few impurities, and the method is economical and very innovative, when compared to a conventional t-butyl alcohol (TBA) dehydration method and methyl t-butyl ether (MTBE) cracking method that use TBA and MTBE, which have low reactivity, and need removal of unreacted reactants or byproducts produced during etherification and cracking through complicated processes including processing using plural columns and washing.

INDUSTRIAL APPLICABILITY

A method of preparing high-purity isobutene using glycol ether, according to the present invention, is useful to separate (prepare) high-purity isobutene from a $C_4$ mixture, in particular $C_4$ raffinate-1 containing isobutene.

The invention claimed is:

1. A method of preparing isobutene, comprising the sequential steps of:
   a) reacting a $C_4$ mixture containing isobutene with glycol in the presence of an acid catalyst to provide a glycol ether, wherein said glycol ether comprises glycol di-t-butyl ether and glycol mono-t-butyl ether, and wherein an amount of glycol di-t-butyl ether is larger than an amount of glycol mono-t-butyl ether;
   b) separating said glycol ether from the unreacted $C_4$ mixture and glycol; and
   c) cracking said glycol ether into isobutene and glycol at a temperature between 50° C. and 300° C. in the presence of a strongly acidic catalyst, wherein the glycol di-t-butyl ether of said glycol ether is completely decomposed.

2. The method according to claim 1, wherein the cracking is performed in a glycol ether cracking reactor or a reactive distillation column.

3. The method according to claim 1, wherein the acid catalyst is a strongly acidic solid ion exchange resin containing a sulfonic acid group.

4. The method according to claim 1, wherein the glycol is a compound represented by Formula 1 below:

<Formula 1>

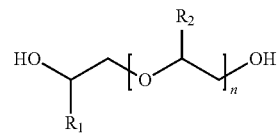

wherein $R_1$ and $R_2$ are each independently a hydrogen atom or a $C_1$-$C_5$ alkyl group, and n is an integer of 0 to 4.

5. The method according to claim 1, wherein the cracking is continuously or non-continuously performed.

6. The method according to claim 1, wherein the $C_4$ mixture of step (a) comprises isobutene in an amount of between 30 wt % and 50 wt %.

7. The method according to claim 1, wherein a molar ratio of glycol to isobutene in step (a) is from 1:1 to 5:1.

* * * * *